United States Patent [19]

Shevade et al.

[11] Patent Number: 5,681,552
[45] Date of Patent: Oct. 28, 1997

[54] CLEAR COSMETIC STICK COMPOSITION CONTAINING A COMBINATION OF ANIONIC AND NON-IONIC SURFACTANTS

[75] Inventors: Makarand Shevade, Plainsboro; Bhalchandra D. Moghe, Scotch Plains; Radhakrishna B. Kasat, Bellemead, all of N.J.

[73] Assignee: The Mennen Company, Morristown, N.J.

[21] Appl. No.: 448,104

[22] Filed: May 23, 1995

[51] Int. Cl.⁶ ............................................. A61K 7/32
[52] U.S. Cl. ................. 424/65; 424/78.02; 424/78.08; 424/78.18; 512/1; 514/944; 514/946
[58] Field of Search ...................... 424/65, 78.02, 424/78.08, 78.18; 512/1; 514/944, 946

[56] References Cited

U.S. PATENT DOCUMENTS

| | | |
|---|---|---|
| 4,122,029 | 10/1978 | Gee et al. |
| 4,151,272 | 4/1979 | Gary et al. |
| 4,265,878 | 5/1981 | Keil |
| 4,268,498 | 5/1981 | Gedeon et al. |
| 4,504,465 | 3/1985 | Sampson et al. |
| 4,759,924 | 7/1988 | Luebbe et al. |
| 4,822,602 | 4/1989 | Sabatelli |
| 5,114,717 | 5/1992 | Kuznitz et al. |
| 5,128,123 | 7/1992 | Brewster et al. ............. 424/65 |
| 5,198,218 | 3/1993 | Kuznitz et al. .............. 424/401 |
| 5,316,761 | 5/1994 | Brazinsky .................... 424/65 |
| 5,424,070 | 6/1995 | Kasat et al. ................. 424/401 |
| 5,458,880 | 10/1995 | Kasat et al. ................. 424/401 |
| 5,462,736 | 10/1995 | Rech et al. .................. 424/401 |
| 5,463,098 | 10/1995 | Giovanniello et al. ........ 424/66 |

FOREIGN PATENT DOCUMENTS

| | | |
|---|---|---|
| 0450597 | 10/1991 | European Pat. Off. . |
| 062338A2 | 4/1994 | European Pat. Off. . |
| WO94/27567 | 12/1994 | WIPO . |

*Primary Examiner*—Terressa Mosley
*Attorney, Agent, or Firm*—Antonelli, Terry, Stout & Kraus, LLP

[57] ABSTRACT

Disclosed are clear, soap-gelled cosmetic (e.g., deodorant) stick compositions, containing alcohol and water, and including a combination of anionic (e.g., sodium laureth-13 carboxylate) and non-ionic (e.g., Ceteareth-55) surfactants as a clarifying agent. The non-ionic surfactants preferably include ethoxylated alcohols, and preferably have an $HLB \geq 24$. The compositions can include various cosmetically active materials, including deodorant active materials (fragrance, Triclosan, etc.). The compositions have superior clarity and maintain superior clarity over extended periods of time, have improved (smoother) glide over the skin and a smoother surface, exhibit reduced syneresis in K-resin and polypropylene dispensing packages, and are easy to manufacture and have high gelling temperatures.

35 Claims, 5 Drawing Sheets

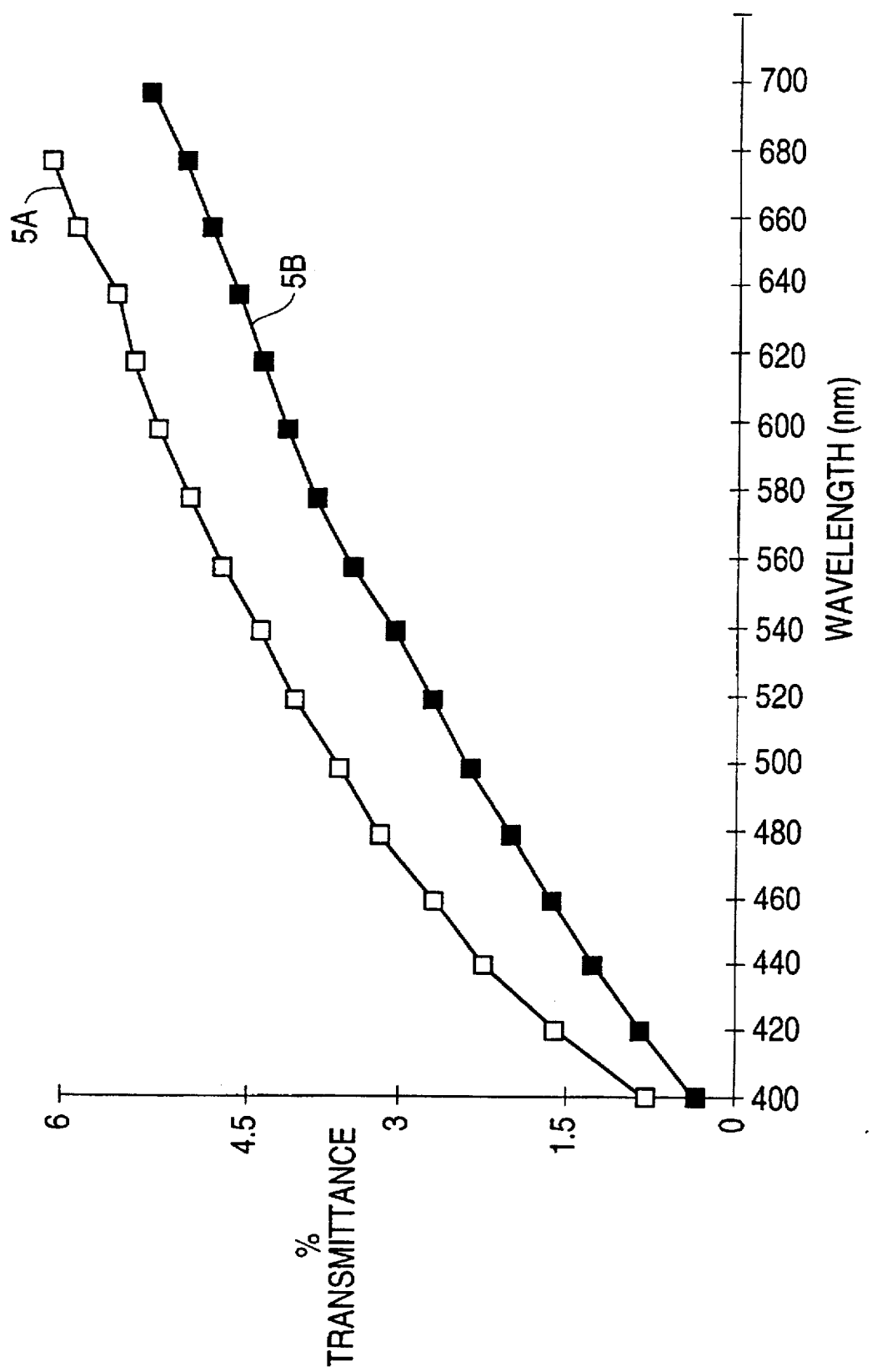

5,681,552

CLEAR COSMETIC STICK COMPOSITION CONTAINING A COMBINATION OF ANIONIC AND NON-IONIC SURFACTANTS

BACKGROUND OF THE INVENTION

The present invention relates to clear stick compositions, e.g., clear cosmetic solid stick compositions such as deodorant solid stick compositions. More specifically, the present invention relates to clear solid stick compositions containing an alcohol (for example, a monohydric alcohol, such as ethanol, or a polyhydric alcohol, such as propylene glycol) and water, and gelled with a soap (for example, an alkali metal salt of a saturated fatty acid, or a mixture of alkali metal salts of saturated fatty acids). In particular, the present invention relates to clear solid stick compositions with superior clarity, so as to achieve an improved appearance, and which retain such superior clarity over an extended period of time (that is, which are stable in their clarity), which have a smooth glide on the skin, which have a smooth surface, and which do not show any syneresis in conventional stick dispensing packages (for example, in packages of K-resin (styrene-butadiene plastic copolymer from Phillips Petroleum Co.).

The present invention is especially related to clear, soap-gelled deodorant stick compositions, that have superior clarity and maintain such superior clarity for extended periods of time, which exhibit a smooth glide on the skin, which have a smooth surface, and which do not exhibit syneresis in the dispensing package, the compositions containing a deodorant active material such as a fragrance and/or an antibacterial agent. However, the present invention is not limited to clear, soap-gelled deodorant stick compositions, but has general applicability to other clear sticks. That is, depending on the cosmetic active ingredient incorporated in the stick composition (for example, a deodorant active ingredient, an insect repellant, a sunscreen, an emollient, etc.), the cosmetic stick composition according to the present invention can be a deodorant stick composition, an insect repellant stick, a sun protection (sunscreen) stick, a skin care stick, etc.

It has been desired to provide a soap-gelled, clear cosmetic stick composition, such as a soap-gelled, clear deodorant solid stick composition, which has excellent cosmetic attributes, and which retains clarity over an extended period of time (that is, has a stable clarity) so as to have a long shelf life. Such clear cosmetic stick composition has widespread consumer appeal. It has been desired to provide such clear cosmetic stick composition which maintains clarity for extended periods of time, e.g., from prior to being purchased by the consumer and until the product has been used up by the consumer. In particular, it has been desired to provide such a clear stick composition, having a long shelf life, which avoids crystals forming in the stick.

A recent product, having widespread consumer appeal, is a clear deodorant stick composition in a clear dispensing package. Such package is made of a plastic, such as K-resin or polypropylene. However, in such packaged deodorant sticks, there is a problem of syneresis. Thus, it is particularly desired to provide a soap-gelled, clear deodorant solid stick composition, provided in a clear dispensing package, which avoids syneresis problems.

It has also been desired to provide a soap-gelled clear cosmetic stick composition, such as a deodorant solid stick composition, which maintains superior clarity over extended periods of time, and which does not exhibit syneresis in the dispensing package; and, moreover, has a smooth surface, and has a smooth glide on the skin.

It has further been desired to provide such soap-gelled clear cosmetic stick composition, which is easy to manufacture, and has a higher gelling temperature than that of conventional cosmetic sticks.

U.S. Pat. No. 5,128,123 to Brewster, et al, the contents of which are incorporated herein by reference in their entirety, discloses cosmetic compositions, in the form of sticks, which are clear and mild, containing (in addition to a polyhydric alcohol having from 2–6 carbon atoms and from 2–6 hydroxyl groups, water, and a soap gelling agent) both (a) an alkoxylate copolymer, and (b) a basic amine clarifying agent present in an effective amount to maintain clarity of the stick. The alkoxylate copolymer has a formula $[A-CH_2CH_2-A]_f(C_2H_4O)_a(C_3H_6O)_b(C_2H_4O)_c(C_3H_6O)_d]_e[H]_g$, where A is nitrogen; a, b, c and d are independently selected integers ranging from 0 to 200 with the proviso that the sum of a, b, c and d is at least about 50; e is an integer from 1 to 4; f is an integer from 0 to 1; and g is an integer from 0 to 4. This patent discloses that the copolymer partially replaces soap as a structurant in the stick. This patent also discloses that when f and e are 0 and 1, respectively, the structure described is a poly(ethylene oxide) (propylene oxide) (ethylene oxide) copolymer. This patent further discloses that the clarifying agent is preferably selected from amino alkanols having from 2–6 hydroxyl groups, particularly effective being the propanol amines.

U.S. Pat. No. 5,128,123 defines what is meant by the term "clear" with respect to the stick composition described therein. Specifically, the term "clear" has its usual dictionary definition; thus, a clear stick, like glass, allows for ready viewing of objects behind it. This patent contrasts clear sticks with translucent sticks, which allow light to pass through but causes the light to be so scattered that it will be impossible to clearly identify objects behind the translucent stick. Thus, in the present art there is a difference between clear, translucent and opaque sticks. This patent goes on to define clear, translucent and opaque sticks based on transmittance of light of wavelengths in the range of 400 to 900 nm through a sample 1 cm thick.

U.S. patent application Ser. No. 08/054,302, filed Apr. 30, 1993, now U.S. Pat. No. 5,458,880, issued Oct. 17, 1995, the contents of which are incorporated herein by reference in their entirety, discloses that by incorporating a sodium salt of a methyl carboxy derivative of ethoxylated lauryl alcohol (for example, sodium laureth-13 carboxylate, as defined in the CTFA International Cosmetic Ingredient Dictionary (4th Ed. 1991)) in a soap-gelled stick composition, a transparent, clear stick, which maintains such transparency and clarity for extended periods of time, can be achieved. This patent application discloses that a transparent, clear deodorant stick composition, gelled utilizing a fatty acid soap gelling agent, can be achieved by incorporating the sodium salt of the methyl carboxy derivative of ethoxylated lauryl alcohol in a stick composition which also includes a deodorant active material (e.g., a fragrance, a bacteriostat, a bacteriocide, etc.). This application discloses that such transparent, clear cosmetic stick composition, e.g., such transparent, clear deodorant stick composition, can be provided and maintained, by incorporating the sodium salt of the methyl carboxy derivative of ethoxylated lauryl alcohol in the composition, even if the gelling agent includes salts of $C_{20}$ and/or $C_{22}$ fatty acids.

Notwithstanding the foregoing, it is still desired to provide a clear stick composition, including (but not limited to) a clear deodorant stick composition, which has superior clarity and maintains such superior clarity over extended periods of time, which is easy to manufacture and has a high gelling temperature, which has a smooth glide on the skin, which has a smooth surface, and which does not exhibit syneresis in a plastic (e.g., polypropylene or K-resin) dispensing container.

SUMMARY OF THE INVENTION

Accordingly, it is an object of the present invention to provide a stick composition (e.g., a cosmetic stick composition such as a deodorant solid stick composition) that is clear, with superior clarity, and which maintains such superior clarity over extended periods of time, in particular, over the shelf life and period of use of the stick composition by a consumer.

It is a further object of the present invention to provide a clear cosmetic stick composition, which has superior clarity even when a cosmetically active material (for example, a deodorant active material, an insect repellant, a sunscreen, an emollient, etc.) is incorporated therein, and which maintains such superior clarity for relatively long periods of time (so as to have a relatively long shelf life as a clear product).

It is a further object of the present invention to provide a clear stick composition, e.g., a clear cosmetic stick composition such as a clear deodorant stick composition, containing alcohol and water, and gelled by a soap (such as alkali metal salts of fatty acids), which has superior clarity, and which maintains superior clarity for long periods of time, and wherein crystals do not form within the composition over these long periods of time.

It is a further object of the present invention to provide a soap-gelled cosmetic solid stick composition that has superior clarity when having cosmetically active materials incorporated therein, that maintains such superior clarity, and that provides a stick product having improved glide (that is, a smooth glide) on the skin.

It is a further object of the present invention to provide a clear, soap-gelled cosmetic stick composition having excellent cosmetic attributes.

It is a further object of the present invention to provide a clear, soap-gelled stick composition that is easy to make, and has a relatively high gelling temperature.

It is a further object of the present invention to provide a clear, soap-gelled solid stick composition that has superior clarity, and which exhibits reduced syneresis when packaged in a dispensing container of K-resin.

It is a further object of the present invention to provide a packaged solid stick composition, e.g., a packaged cosmetic solid stick composition such as a packaged deodorant solid stick composition, wherein the composition is clear and the dispensing package, in which the composition is packaged, is also clear, the dispensing package being made of K-resin, and wherein the composition exhibits reduced syneresis when in the dispensing package.

It is a further object of the present invention to provide a clear, soap-gelled deodorant stick composition having deodorant active material incorporated therein, which can be applied, for example, to axillary regions of the human body to reduce or avoid axillary malodor.

It is a still further object of the present invention to provide a clear deodorant stick composition, having deodorant active materials incorporated therein, that has superior clarity and maintains such superior clarity over extended periods of time, that has improved (a smoother) glide on the skin and has a smooth surface, that is easy to manufacture and has a high gelling temperature, and that exhibits reduced syneresis in a dispensing package (for example, a clear dispensing package) of K-resin.

The foregoing objects are achieved, according to the present invention, by incorporating, in the soap-gelled stick composition containing alcohol and water, a combination of at least one anionic surface active agent (surfactant) and at least one non-ionic surface active agent (surfactant), the surface active agents being incorporated in the composition in an amount so as to provide a clarified (i.e., clear) composition. More particularly, compositions of the present invention include alcohol, water, a soap gelling agent, and a mixture of at least one anionic surface active agent and at least one non-ionic surface active agent. Illustratively, but not limiting, the compositions include some of each of the anionic and non-ionic surface active agents (surfactants), and can contain up to and including 10% by weight, of the total weight of the composition, of each of the anionic surfactant and non-ionic surfactant. A preferred minimum amount of non-ionic surfactant, and a preferred minimum amount of anionic surfactant, are each 2.0% by weight, of the total weight of the composition.

By non-ionic surface active agents (surfactants), we mean surfactants with uncharged hydrophilic head groups. These non-ionic surfactants include polyethylene oxide, alcohols and other polar groups. Straight chain primary alkoxylated alcohols, including (but not limited to) straight chain primary ethoxylated alcohols; and alkoxylate polymers such as alkoxylate copolymers and alkoxylate homopolymers, including (but not limited to) ethoxylate homopolymers, can be used as non-ionic surfactants in the composition of the present invention. Preferably, the non-ionic surfactants contain polyethylene oxide groups.

By anionic surface active agents (surfactants), we mean surfactants with negatively charged head groups. These anionic surfactants include, in general, long-chain fatty acids, sulfosuccinates, alkyl sulfates, phosphates, and sulfonates.

The above-mentioned U.S. patent application Ser. No. 08/054,302, filed Apr. 30, 1993, describes incorporating sodium laureth-13 carboxylate in soap-gelled cosmetic sticks, to provide clear soap-gelled cosmetic sticks. Sodium laureth-13 carboxylate is an anionic surfactant. By adding, in addition to anionic surfactants, non-ionic surfactants, the clarity of the composition is further improved, so as to provide a soap-gelled stick composition having superior clarity, and which maintains such superior clarity.

Optimally, the non-ionic surfactants incorporated in the combination of surfactants have a hydrophile-lipophile balance (HLB) of at least 24.

Preferably, the soap gelling agent of the composition of the present invention contains salts of saturated or unsaturated fatty acids having a carbon chain length in the range of $C_{12}$–$C_{22}$, with at least some of the salts being salts of fatty acids having carbon chain length of $C_{20}$ and/or $C_{22}$. Utilizing, for example, sodium salts of long-chain saturated fatty acids of carbon chain length of $C_{20}$ and/or $C_{22}$ provides a product having a relatively higher gelling temperature and improved stability.

However, a problem arises in utilizing such soap-gelling agent that includes salts of fatty acids having carbon chain lengths of $C_{20}$ and/or $C_{22}$, in that there is increased crystallization in the stick composition over extended periods of time, disadvantageously affecting the clarity of the stick composition. Such crystallization can be reduced when incorporating the combination of anionic and non-ionic surfactants in the stick composition, according to the present invention.

The clear solid stick composition according to the present invention can include various active materials, including sunscreens, deodorant active materials, insect repellents, skin care materials (e.g., emollients), etc., to provide clear cosmetic solid stick compositions. These active materials can be incorporated to the extent that they do not disadvantageously affect clarity of the final product. It is preferred that materials which reduce clarity are not incorporated in the composition of the present invention.

As for various active materials which can be incorporated in the stick composition according to the present invention, and amounts of these materials, see U.S. Pat. No. 5,128,123, the contents of which have previously been incorporated herein by reference in their entirety.

Compositions according to the present invention can include various additional materials conventionally included in cosmetic stick compositions, to the extent that these additional materials do not disadvantageously effect clarity of the stick product. Various additional materials incorporated in stick compositions are disclosed in U.S. Pat. No. 5,128,123, the contents of which have previously been incorporated herein by reference in their entirety, and in U.S. Pat. No. 4,759,924 to Luebbe, et al, the contents of which are incorporated herein by reference in their entirety. The additional materials can include, illustratively (and not limiting), polyols, fatty alcohols, alkanolamide, color (for example, dyes), essential oils, soluble inorganic salts of sodium and potassium, etc.

Accordingly, by the present invention, which incorporates a combination (e.g., mixture) of anionic and non-ionic surfactants in the soap-gelled stick composition containing water and alcohol, a solid stick composition is achieved that has superior clarity, and maintains superior clarity over relatively long periods of time; has excellent cosmetic properties; has a smooth surface; has a smooth glide on the skin; is easy to make, and has a relatively high gelling temperature; and avoids syneresis when packaged in conventional stick dispensing packages, e.g., of K-resin or polypropylene, including where the composition is packaged in a clear package of, e.g., K-resin. Moreover, various cosmetic active ingredients, such as deodorant active materials, can be incorporated in the composition, so as to provide, for example, deodorant stick compositions having superior clarity and that retain superior clarity over long periods of time (have stable clarity) and also satisfy the other objectives discussed previously.

BRIEF DESCRIPTION OF THE DRAWINGS

FIG. 5 is a graph of percent transmittance of light, as a function of wavelength, through a composition according to the present invention and through a composition containing only an anionic surfactant, where each of the compositions has been subjected to three freeze/thaw cycles.

DETAILED DESCRIPTION OF THE INVENTION

Figure 1:
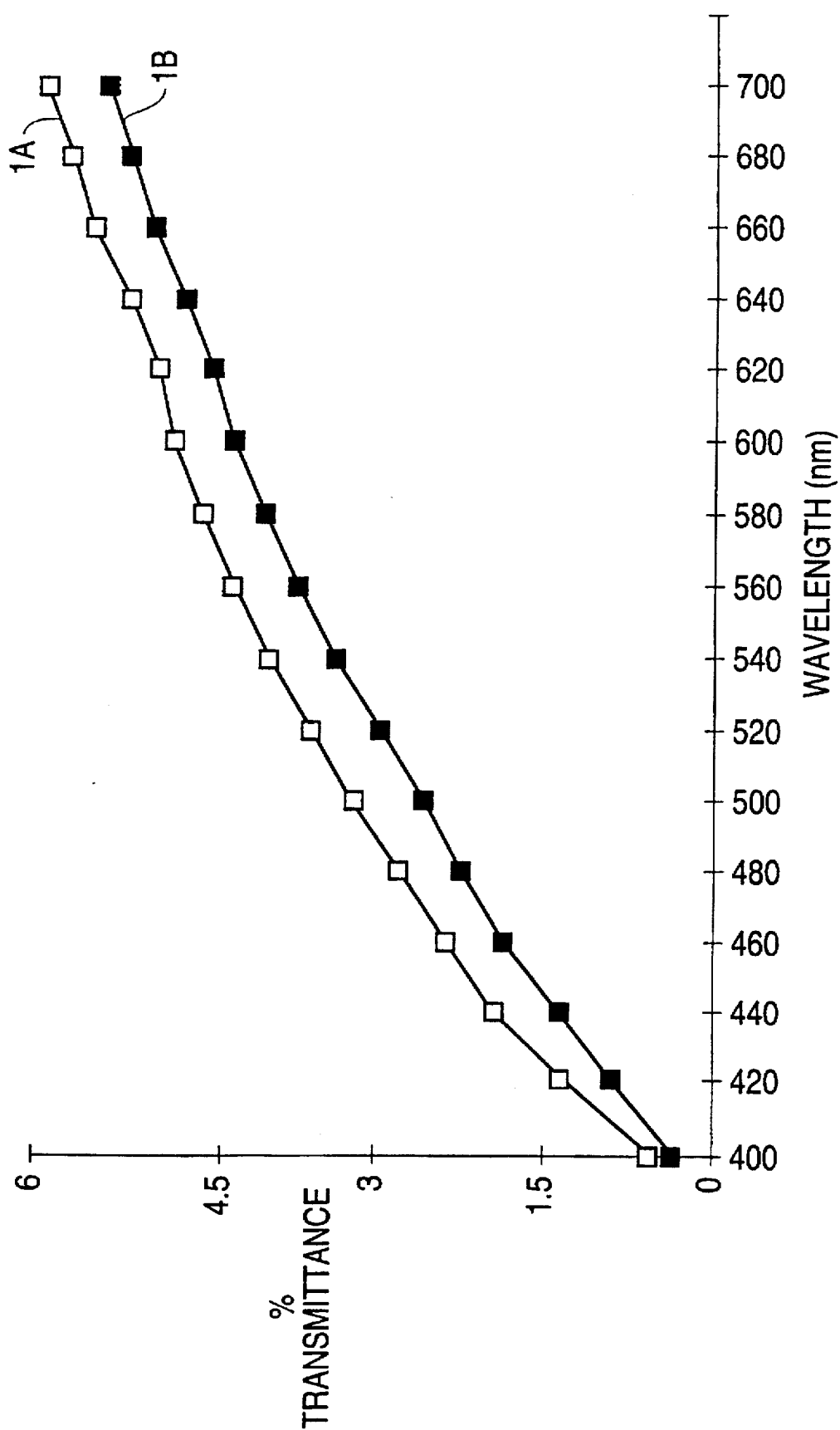
FIG. 1 is a graph showing the percent transmittance of light, as a function of wavelength, through a composition according to the present invention and through a composition containing only an anionic surfactant, upon initially forming each of the compositions.

While the present invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Thus, while the description is most specific with respect to clear deodorant stick compositions, the present invention is not limited to deodorant stick compositions, but includes within its scope various cosmetic products, depending on the cosmetically active material incorporated in the stick composition.

Throughout the present disclosure, where compositions are described as including or comprising specific components or materials, it is contemplated by the inventors that compositions of the present invention also consist essentially of, or consist of, the recited components or materials. Accordingly, throughout the present disclosure any described composition of the present invention can consist essentially of, or consist of, the recited components or materials.

Throughout the present disclosure, various of the components of the disclosed compositions are denoted by their name in the CTFA International Cosmetic Ingredient Dictionary (4th Ed. 1991), the contents of which are incorporated herein by reference in their entirety.

The present invention is directed, in general, to clear stick compositions. By clear, we mean the usual dictionary definition of this term. Thus, a clear stick composition, like glass, allows for ready viewing of objects behind it. By contrast, a translucent stick composition, although allowing light to pass through, causes the light to be so scattered that it will be impossible to clearly identify objects behind the translucent stick. Opaque sticks do not permit light to pass therethrough. Thus, according to the present invention, there is a distinction between, e.g., "clear" and "translucent" sticks.

The present invention contemplates clear stick compositions (for example, clear cosmetic stick compositions, such as clear deodorant solid stick compositions) containing alcohol and water, and gelled with salts (soaps) of fatty acids (saturated or unsaturated fatty acids), the compositions further including a combination of at least one anionic surface active agent (surfactant) and at least one non-ionic surface active agent (surfactant), for providing a composition having superior clarity.

An illustrative group of anionic surfactants that can be used according to the present invention are the sodium salts of methyl carboxy derivatives of ethoxylated lauryl alcohol; a specific sodium salt of methyl carboxy derivative of ethoxylated lauryl alcohol, useful in the present invention, is sodium laureth-13 carboxylate. However, the anionic surfactant is not limited to these illustrative compounds. The anionic surfactant can be incorporated in the compositions in an amount of more than 0, and up to and including 10% by weight, of the total weight of the composition, preferably 2%–8% by weight of the total weight of the composition, most preferably 4%–6% by weight of the total weight of the composition.

The non-ionic surfactant is preferably a straight chain primary alkoxylated alcohol, more preferably a straight chain primary ethoxylated alcohol. The non-ionic surfactant can be an alkoxylate homopolymer, preferably an ethoxylate homopolymer. Illustrative non-ionic surfactants for use according to the present invention include Ceteareth-55, C14-15 Pareth-2.25 and C14-15 Pareth-13; these illustrative non-ionic surface active agents are not limiting. The non-ionic surfactants according to the present invention desirably have a hydrophile-lipophile balance of at least 24.

Illustratively, the non-ionic surfactants are included in the composition in an amount of more than 0, and up to and including 10% by weight, of the total weight of the composition. A preferred range for amount of non-ionic surfactant is 2%–8% by weight, of the total weight of the composition, and a most preferred amount of non-ionic surfactant is 2%–4% by weight, of the total weight of the composition.

The alcohol included in the solid stick composition of the present invention can be a monohydric and/or polyhydric alcohol (for example, ethanol as a monohydric alcohol, and propylene glycol and/or dipropylene glycol as polyhydric alcohols). The alcohol can be a mixture of alcohols, including a mixture of monohydric and polyhydric alcohols, or a mixture of monohydric alcohols or a mixture of polyhydric alcohols. Various polyhydric alcohols which can be used in soap-gelled alcohol-and water-containing stick compositions are described in U.S. Pat. No. 4,759,924, the contents of which have previously been incorporated herein by reference in their entirety, and can also be used in the present invention.

A necessary component of the cosmetic stick composition according to the present invention is a soap gel-forming agent. Alkali metal salts of fatty acids of carbon chain length $C_{12}$–$C_{22}$, e.g., sodium salts of saturated fatty acids having the above-mentioned carbon chain length, can be utilized as the gel-forming agent. Preferred gel-forming agents according to the present invention include sodium salts (that is, soaps) of relatively long-length-carbon-chain saturated fatty acids (for example, sodium salts of saturated fatty acids having carbon chain lengths of $C_{20}$ and/or $C_{22}$). The fatty acid portions of the soap can include a mixture of different saturated fatty acids of carbon chain length in the range $C_{12}$–$C_{22}$, preferably including some $C_{20}$ and/or $C_{22}$. By utilizing such relatively long-carbon-chain-length fatty acids, a product is provided having a relatively high melting temperature, and, correspondingly, relatively greater stability.

Preferred gel-forming agents according to the present invention include mixtures of sodium fatty acid soaps, having different fatty acid portions. For example, the soap gel-forming agent can be a mixture of sodium laurate, sodium myristate, sodium palmitate, sodium stearate, sodium arachidate, and sodium behenate, with the sodium fatty acid soaps respectively preferably having the following distribution:

| FATTY ACID DISTRIBUTION | |
|---|---|
| Fatty Acid Soap | % (By Weight, of the Soap Mixture) |
| Sodium laurate | 2% |
| Sodium myristate | 4–7% |
| Sodium palmitate | 35–44% |
| Sodium stearate | 31–44% |
| Sodium arachidate | 7–9% |
| Sodium behenate | 8–10% |

This mixture of sodium fatty acid soaps, having the desired distribution, can be provided in any number of ways known in the art. For example, pure sodium laurate, pure sodium myristate, etc., can be mixed together in desired proportions. Or difference mixtures of sodium fatty acid soaps (for example, commercial grade sodium stearate, containing sodium stearate, sodium palmitate, etc., and another mixture of sodium fatty acid soaps) can be combined to provide the desired distribution.

The foregoing fatty acid soap distribution of the soap gel-forming agent is illustrative and not limiting of the present invention.

Illustratively, and not limiting, the clear stick composition according to the present invention can include the following amounts (in percent by weight, of the total weight of the composition) of other components than the anionic and non-ionic materials:

alcohol (e.g., propylene glycol):55–80% water: 9–25% soap: 4–10%

Other materials can be included in the clear stick compositions according to the present invention, and include various cosmetically active materials so as to provide clear cosmetic stick compositions. For example, and not limiting, cosmetic stick compositions according to the present invention can include cosmetically active materials such as deodorant active materials (including fragrances and antibacterial agents), sunscreens, skin conditioners, nail conditioners and the like. To the extent that these materials, and amounts thereof, do not unsatisfactorily affect clarity, and, where appropriate, such materials can safely be applied to the human body, these materials can be included in the clear cosmetic stick compositions of the present invention.

As indicated previously, compositions according to the present invention have use as underarm deodorant compositions (e.g., by application to axillary regions of the human body), when having deodorant active materials incorporated in the composition. Various deodorant active materials which can be included in the compositions according to the present invention, and amounts of these materials, are described in U.S. Pat. No. 4,759,924, the contents of which have previously been incorporated herein by reference in their entirety, and include (but are not limited to) fragrances (e.g., perfumes, including deoperfumes) and antibacterial agents (e.g., bacteriostats and bactericides), among others. For example, a deodorant active material useful as an antibacterial agent in the present invention is 2,4,4'-trichloro-2'-hydroxydiphenylether (CTFA Name: Triclosan). An antibacterial agent such as Triclosan is not a required component of the composition, even where the composition is a deodorant stick composition to be applied to the axillary regions to combat body malodor.

Other ingredients such as dyes, pigments, coloring agents, etc., which do not disadvantageously effect the clarity of the solid stick compositions of the present invention, can desirably be incorporated in the soap-gelled compositions of the present invention, in amounts as conventionally incorporated and as discussed in U.S. Pat. No. 4,759,924.

The compositions according to the present invention are manufactured by processing techniques conventional in the art. A desirable feature of the present invention is that the stick compositions of the present invention have a higher gelling temperature than that of conventional stick compositions (e.g., conventional clear stick compositions), and need not be cooled to as low a level prior to gelling. For example, compositions according to the present invention have a gelling temperature in the range of 53°–55° C., as compared to conventional clear sticks having a gelling temperature less than 50° C.

Specifically, the solid components of the compositions are melted, and these melted components are mixed. Preferably, the fragrance (if any) is added close to the end of the manufacturing process (for example, is the last component added), with the previously mixed components being cooled to a lower temperature (while still maintaining a melt) prior to adding the fragrance, so as to limit any volatilization of the fragrance. While still in the liquid state, the composition is filled in a dispensing package (as conventional in the art) and then cooled to solidify the product in the package.

The present invention, containing a combination of anionic and non-ionic surfactants, provides an additional advantage of reducing syneresis in the dispensing package. There have been difficulties in previously proposed compositions, in that the compositions would exhibit syneresis when in a package of K-resin or polypropylene, which are conventionally used materials for dispensing packages. The present invention avoids this problem of syneresis, in either polypropylene or K-resin packages.

A preferred embodiment of the present invention utilizes a dispensing package of, e.g., K-resin, as a clear dispensing package. Utilizing a clear dispensing package of K-resin, with the clear deodorant stick composition according to the present invention therein, provides a product having increased consumer appeal.

The compositions according to the present invention are utilized by conventional techniques. For example, when utilizing the compositions according to the present invention as an axillary deodorant solid stick, having deodorant active materials (such as Triclosan and/or a fragrance) incorporated therein, the solid stick product is elevated out of the dispensing package so as to expose the end of the stick product, and the exposed portion of the stick product is then rubbed against, e.g., the axillary region of the human body so as to deposit the deodorant active materials on the skin in the axillary region, so as to provide deodorant protection.

While, in the foregoing, the present invention has been described in terms of a deodorant solid stick composition for use in axillary regions, the present invention is not so limited; and the cosmetic stick composition according to the present invention has various uses depending on the active material incorporated therein, including (but not limited to) as a deodorant for other parts of-the body, sun protection stick, insect repellant, skin softener, etc.

In the following, a specific example within the scope of the present invention, together with a comparative example outside the scope of the present invention, will be set forth. In the following, the stated percentages are percentages by weight, of the stated component, relative to the total weight of the composition. The names utilized are the CTFA names for the ingredients, where applicable.

|  | Example 1 W/W % | Comparative Example 1 W/W % |
| --- | --- | --- |
| Propylene Glycol | 70.00 | 73.00 |
| Triclosan | 0.25 | 0.25 |
| Sodium Stearate | 6.00 | 6.00 |
| D.I. Water | 13.56 | 13.56 |
| Sodium laureth-13 Carboxylate | 6.00 | 6.00 |
| Ceteareth-55 | 3.00 | — |
| Fragrance | q.a | q.a |

In the foregoing, Example 1 falls within the scope of the present invention, while Comparative Example 1 contains an anionic surfactant but no non-ionic surfactant. Clarity of the sticks formed in Example 1 and Comparative Example 1 was assessed by measuring light transmitted through a 2 cm section of the stick in a wavelength range from 400 to 700 nm, using a Milton Roy Color Mate colorimeter. The sticks were evaluated initially and after accelerated aging for three weeks, at 77° F., 100° F. and 120° F. Moreover, clarity was also assessed after three freeze/thaw cycles.

Figure 2:
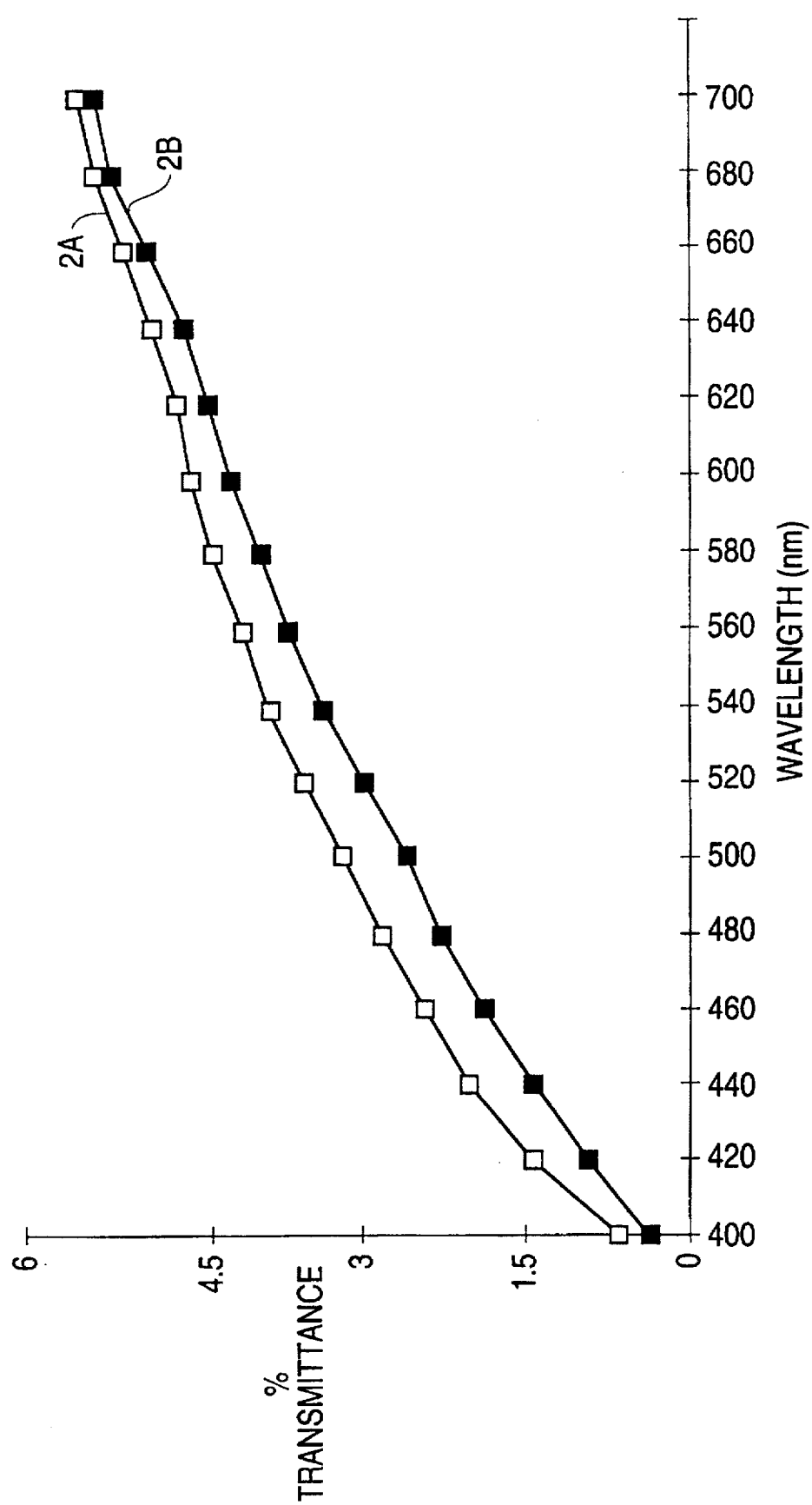
FIG. 2 is a graph of percent transmittance of light, as a function of wavelength, through a composition according to the present invention and through a composition containing only an anionic surfactant, where each of the compositions has been stored for three weeks at 77° F.
Figure 3:
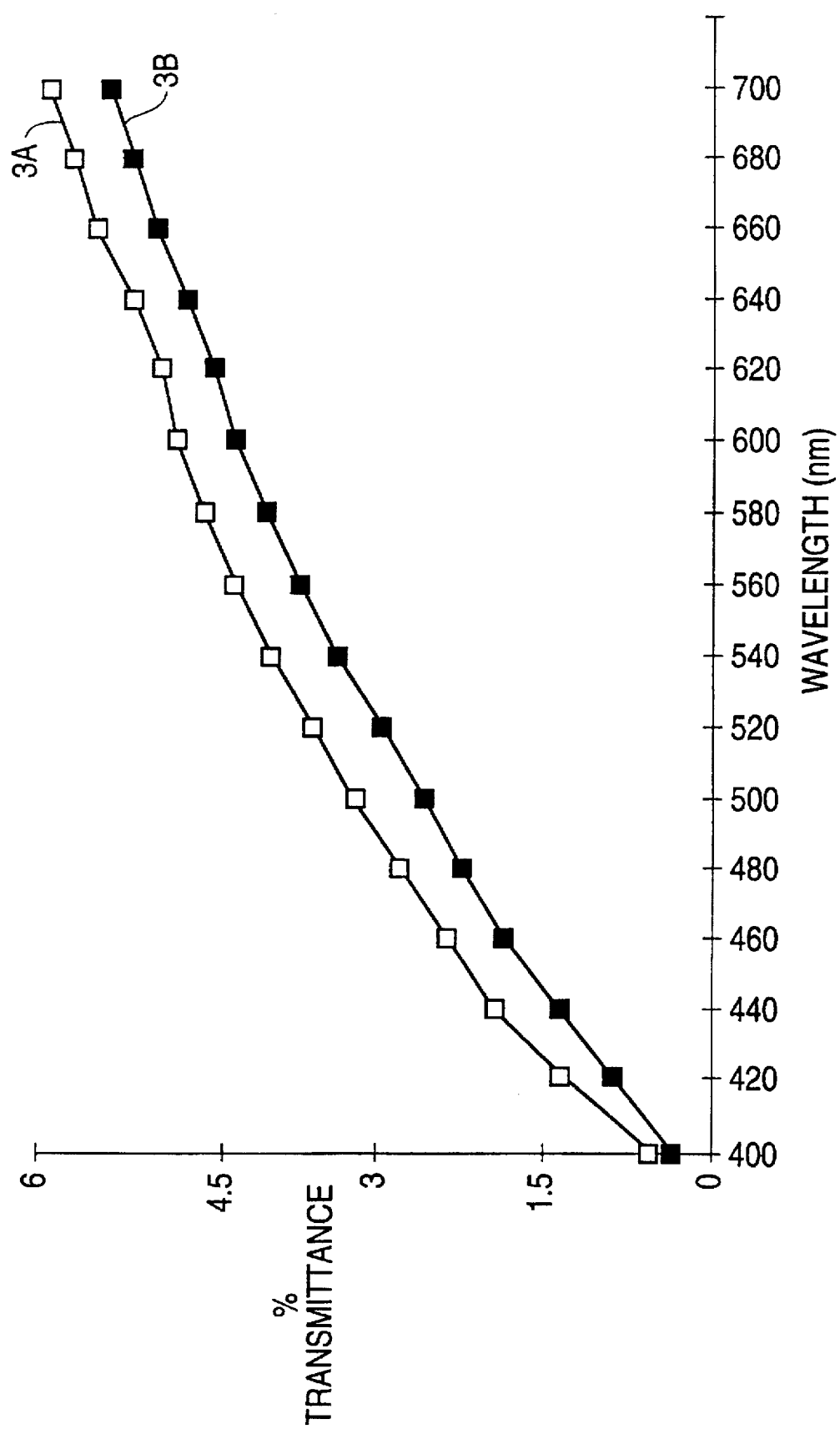
FIG. 3 is a graph of percent transmittance of light, as a function of wavelength, through a composition according to the present invention and through a composition containing only an anionic surfactant, where each of the compositions has been stored for three weeks at 100° F.
Figure 4:
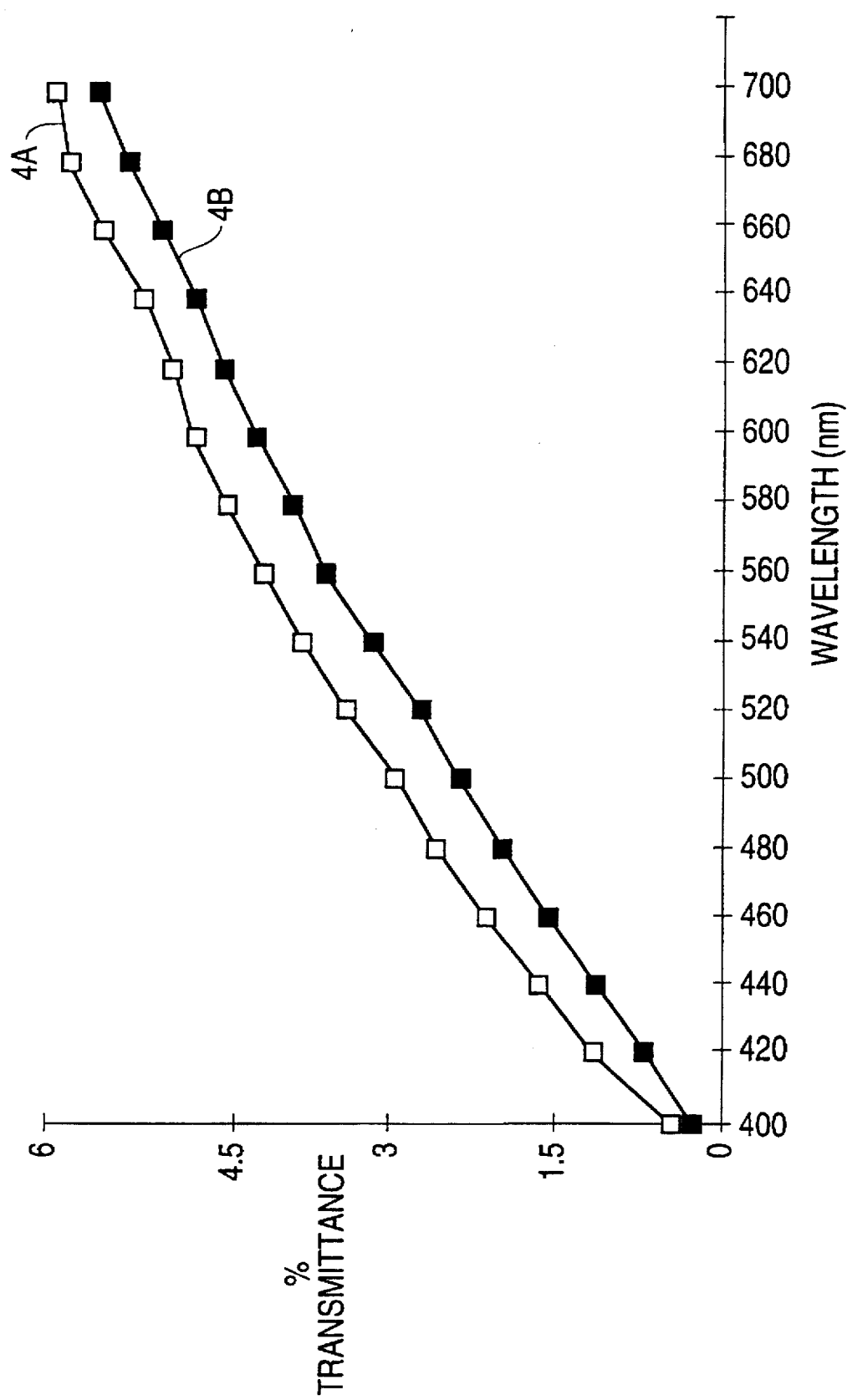
FIG. 4 is a graph of percent transmittance of light, as a function of wavelength, through a composition according to the present invention and through a composition containing only an anionic surfactant, where each of the compositions has been stored for three weeks at 120° F.

The results of the evaluation are shown in FIGS. 1–5. Thus, FIGS. 1–5 respectively represent the results of the initial evaluation, evaluation after accelerated aging for three weeks at 77° F., at 100° F. and at 120° F., and after three freeze/thaw cycles. In these figures, curves 1A, 2A, 3A, 4A and 5A represent the results of evaluating the composition according to the present invention, and 1B, 2B, 3B, 4B and 5B represent the results of the evaluation of the composition of Comparative Example 1. As seen, the present invention provides a very clear composition, both initially and after accelerated aging for three weeks at various temperatures, and after three freeze/thaw cycles, having superior clarity as compared to the composition containing only the anionic surface active agent.

In addition to the advantages in clarity, the composition according to the present invention, utilizing the combination of anionic and non-ionic surface active agents, does not show any syneresis in either polypropylene or K-resin packages, unlike the composition of Comparative Example 1; and, moreover, has a significantly smoother surface than that of the composition of Comparative Example 1.

Accordingly, by including the combination of anionic and non-ionic surfactants as part of a stick composition containing alcohol and water, and gelled with a soap gelling agent, according to the present invention, a clear stick composition with superior clarity, and which maintains superior clarity over extended periods of time, is achieved. Moreover, such stick has improved (smoother) glide on, e.g., the skin during application, and also avoids syneresis when utilized in a dispensing package of K-resin or polypropylene. In addition, such stick is easy to manufacture, and has a higher gelling temperature than that of conventional soap-gelled sticks. Furthermore, various cosmetically active materials, including deodorant active materials, such as conventional deodorant active materials, can be incorporated in the stick composition, so as to provide, e.g., a clear deodorant stick, while maintaining the aforementioned good properties.

Attention is directed to the concurrently filed U.S. patent application of LaTonya K. Kilpatrick-Liverman, Andrea Motyka, Bhalchandra D. Moghe, Radhakrishna B. Kasat and Makarand Shevade for "Clear Cosmetic Stick Composition" (Attorney Docket No. 851.33531X00), U.S. patent application Ser. No. 08/448,101, filed May 23, 1995, the contents of which are incorporated herein by reference in their entirety.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A clear stick composition, comprising alcohol and water, and a soap gelling agent, the soap gelling agent being included in an amount so as to gel and to form the stick composition, the composition further including, as a clarifying agent, a combination of both (a) at least one anionic surface active agent and (b) at least one non-ionic surface active agent, the at least one non-ionic surface active agent including a straight chain primary alkoxylated alcohol, other than nonoxynol-10, ceteareth-12, ceteareth-20, ceteareth-30, PEG-40 hydrogenated castor oil, PEG-60 hydrogenated castor oil, PPG-2 ceteareth-9, oleth-10-, oleth-5 and PEG-40 castor oil, the combination of anionic and non-ionic surface active agents being included in the composition in an amount so as to provide a clear stick composition, the at least one anionic surface active agent being included in the composition in an amount of 2–8% by weight, of the total weight of the composition, and the at least one non-ionic surface active agent being included in the composition in an amount of 2–8% by weight, of the total weight of the composition.

2. A clear stick composition according to claim 1, wherein the composition further includes a deodorant effective amount of a deodorant active material, whereby the composition is a clear deodorant stick composition.

3. A clear stick composition according to claim 2, wherein said deodorant active material is at least one selected from the group consisting of fragrances and antibacterial agents.

4. A clear stick composition according to claim 1, wherein the alcohol includes propylene glycol, and the soap gelling agent includes alkali metal salts of fatty acids.

5. A clear stick composition according to claim 4, wherein the composition includes, in percent by weight of the total weight of the composition, 55–80% propylene glycol, 9–25% water and 4–10% soap gelling agent.

6. A clear stick composition according to claim 1, wherein the composition includes, in percent by weight of the total weight of the composition, 4–6% of the at least one anionic surface active agent and 2–4% of the at least one non-ionic surface active agent.

7. A clear stick composition according to claim 1, wherein said straight chain primary alkoxylated alcohol is a straight chain primary ethoxylated alcohol.

8. A clear stick composition according to claim 1, wherein said at least one non-ionic surface active agent has a hydrophile-lipophile balance of at least 24.

9. A clear stick composition according to claim 8, wherein the straight chain primary alkoxylated alcohol is a straight chain primary ethoxylated alcohol.

10. A clear stick composition according to claim 8, wherein the at least one anionic surface active agent includes sodium laureth-13 carboxylate.

11. A clear stick composition according to claim 10, wherein the at least one non-ionic surface active agent is selected from the group consisting of Ceteareth-55, C14-15 Pareth-2.25 and C14-15 Pareth-13.

12. A clear stick composition according to claim 11, wherein the at least one non-ionic surface active agent includes Ceteareth-55.

13. A clear stick composition according to claim 7, wherein the composition further includes a deodorant effective amount of a deodorant active material, whereby the composition is a clear deodorant stick composition.

14. A clear deodorant stick composition according to claim 13, wherein said deodorant active material is at least one selected from the group consisting of fragrances and antibacterial agents.

15. A clear stick composition according to claim 1, wherein the composition further includes a deodorant effective amount of a deodorant active material, whereby the composition is a clear deodorant stick composition.

16. A clear deodorant stick composition according to claim 15, wherein said deodorant active material is at least one selected from the group consisting of fragrances and antibacterial agents.

17. A clear stick composition according to claim 1, wherein the at least one anionic surface active agent is selected from the group consisting of long-chain fatty acids, sulfosuccinates, alkyl sulfates, phosphates and sulfonates.

18. A clear stick composition according to claim 1, wherein the at least one non-ionic surface active agent includes polyethylene oxide groups.

19. A clear stick composition according to claim 1, wherein the soap gelling agent includes salts of fatty acids, the fatty acids having a carbon chain length in a range of $C_{12}$–$C_{22}$, at least some of the salts being salts of fatty acids having carbon chain length of at least one of $C_{20}$ and $C_{22}$.

20. A clear stick composition according to claim 1, wherein the at least one anionic surface active agent includes a sodium salt of methyl carboxy derivatives of ethoxylated lauryl alcohol.

21. A clear stick composition according to claim 1, wherein the soap gelling agent includes sodium laurate, sodium myristate, sodium palmitate, sodium stearate, sodium arachidate and sodium behenate.

22. A packaged clear deodorant stick composition, comprising the clear deodorant stick composition of claim 15 in a dispensing package, wherein the dispensing package is made of a styrene-butadiene copolymer.

23. A packaged clear deodorant stick composition according to claim 22, wherein the dispensing package is clear.

24. A packaged clear stick composition, comprising the clear stick composition of claim 1 in a dispensing package, wherein the dispensing package is made of a styrene-butadiene copolymer.

25. A packaged clear deodorant stick composition according to claim 24, wherein the dispensing package is clear.

26. A method of reducing body malodor, comprising rubbing the clear deodorant stick composition of claim 15 on axillary regions of a human body.

27. A method of reducing body malodor, comprising rubbing the clear deodorant stick composition of claim 13 on axillary regions of human body.

28. A method of reducing body malodor, comprising rubbing the clear deodorant stick composition of claim 2 on axillary regions of a human body.

29. A clear stick composition, comprising alcohol and water, and a soap gelling agent, the soap gelling agent being included in an amount so as to gel and to form the stick composition, the composition further including, as a clarifying agent, a combination of both (a) at least one anionic surface active agent and (b) at least one non-ionic surface active agent, the at least one non-ionic surface active agent including an alkoxylate homopolymer, other than nonoxynol-10, ceteareth-12, ceteareth-20, ceteareth-30, PEG-5 cocamide, PEG-40 hydrogenated castor oil, PEG-60 hydrogenated castor oil, oleth-5, oleth-10, PEG-40 castor oil, polysorbate 20, polysorbate 60, polysorbate 80 and PEG-8 stearate, the combination of anionic and non-ionic surface active agents being included in the composition in an amount so as to provide a clear stick composition, the at least one anionic surface active agent being included in the composition in an amount of 2–8% by weight, of the total weight of the composition, and the at least one non-ionic surface active agent being included in the composition in an amount of 2–8% by weight, of the total weight of the composition.

30. A clear stick composition according to claim 29, wherein the composition includes, in percent by weight of the total weight of the composition, 4–6% of the at least one anionic surface active agent and 2–4% of the at least one non-ionic surface active agent.

31. A clear stick composition according to claim 29, wherein said alkoxylate homopolymer is an ethoxylate homopolymer.

32. A clear stick composition according to claim 29, wherein said at least one non-ionic surface active agent has a hydrophile-lipophile balance of at least 24.

33. A clear stick composition, comprising alcohol and water, and a soap gelling agent, the soap gelling agent being included in an amount so as to gel and to form the stick composition, the composition further including, as a clarifying agent, a combination of both (a) at least one anionic surface active agent and (b) at least one non-ionic surface active agent, the at least one non-ionic surface active agent having a hydrophile-lipophile balance of at least 24, the combination of anionic and non-ionic surface active agents being included in the composition in an amount so as to provide a clear stick composition.

34. A clear stick composition according to claim 33, wherein the at least one anionic surface active agent and the at least one non-ionic surface active agent are each included in the composition in an amount of 2–8% by weight, of the total weight of the composition.

35. A clear stick composition according to claim 34, wherein the composition includes, in percent by weight of the total weight of the composition, 4–6% of the at least one anionic surface active agent and 2–4% of the at least one non-ionic surface active agent.

* * * * *